United States Patent [19]

Theissen

[11] 4,164,410
[45] * Aug. 14, 1979

[54] ESTERS OF SUBSTITUTED PHENOXYBENZOIC ACIDS, COMPOSITIONS OF THE SAME AND HERBICIDAL USE THEREOF

[75] Inventor: Robert J. Theissen, Bridgewater, N.J.

[73] Assignee: Mobil Oil Corp., New York, N.Y.

[*] Notice: The portion of the term of this patent subsequent to Mar. 28, 1989, has been disclaimed.

[21] Appl. No.: 903,366

[22] Filed: May 5, 1978

Related U.S. Application Data

[63] Continuation of Ser. No. 837,957, Sep. 29, 1977, which is a continuation of Ser. No. 702,367, Jul. 2, 1976, which is a continuation-in-part of Ser. No. 617,569, Sep. 29, 1975, Pat. No. 3,979,437, which is a continuation of Ser. No. 398,610, Sep. 19, 1973, Pat. No. 3,941,830, which is a continuation of Ser. No. 114,712, Feb. 11, 1971, Pat. No. 3,784,635, which is a continuation-in-part of Ser. No. 819,412, Apr. 25, 1969, Pat. No. 3,652,645, said Ser. No. 702,367, is a continuation-in-part of Ser. No. 545,232, Jan. 29, 1975, Pat. No. 4,002,662, which is a continuation-in-part of Ser. No. 398,610.

[51] Int. Cl.$^2$ .................. A01N 9/12; A01N 9/14; C07C 121/64; C07C 79/46
[52] U.S. Cl. ............................ 71/98; 71/103; 71/105; 71/111; 260/465 D; 560/12; 560/13; 560/17; 560/21
[58] Field of Search ................ 71/107, 98, 103, 105, 71/111; 560/21, 12, 13, 17; 260/465 D

[56] References Cited

U.S. PATENT DOCUMENTS

| | | | |
|---|---|---|---|
| 3,423,470 | 1/1969 | Rohr et al. | 260/612 |
| 3,463,639 | 8/1969 | Baltazzi | 260/559 R |
| 3,475,427 | 10/1969 | Blank et al. | 260/244 |
| 3,652,645 | 3/1972 | Theissen | 71/115 X |
| 3,776,715 | 12/1973 | Theissen | 71/115 X |
| 3,784,635 | 1/1974 | Theissen | 71/105 X |
| 3,798,276 | 3/1974 | Bayer et al. | 260/612 R |
| 3,812,184 | 5/1974 | Theissen | 71/115 X |
| 3,839,444 | 10/1974 | Theissen | 260/559 R |
| 3,873,302 | 3/1975 | Theissen | 71/115 |
| 3,873,303 | 3/1975 | Theissen | 71/118 |
| 3,907,866 | 9/1975 | Theissen | 71/111 X |
| 3,928,416 | 12/1975 | Bayer et al. | 71/105 |
| 3,929,455 | 12/1975 | Theissen | 71/115 |
| 3,941,830 | 3/1976 | Theissen | 560/21 |
| 3,953,489 | 4/1976 | Tamura et al. | 260/455 R |
| 3,979,437 | 9/1976 | Theissen | 260/465 D X |
| 3,983,168 | 9/1976 | Theissen | 260/520 E X |
| 4,001,005 | 1/1977 | Theissen | 71/108 |
| 4,002,662 | 1/1977 | Theissen | 71/105 X |
| 4,015,975 | 4/1977 | Tamura et al. | 71/100 |
| 4,046,798 | 9/1977 | Bayer et al. | 260/465 D |
| 4,063,929 | 12/1977 | Bayer et al. | 71/115 |
| 4,070,178 | 1/1978 | Johnson et al. | 560/21 X |
| 4,093,446 | 6/1978 | Bayer et al. | 560/21 X |

Primary Examiner—Joseph Paul Brust
Attorney, Agent, or Firm—C. A. Huggett; H. S. Trigg; M. G. Gilman

[57] ABSTRACT

2-Nitro-5-(substituted-phenoxy)benzoic acids and esters, salts, amides, and acyl halides thereof comprise a class of compounds that are highly effective herbicides.

3 Claims, No Drawings

ESTERS OF SUBSTITUTED PHENOXYBENZOIC ACIDS, COMPOSITIONS OF THE SAME AND HERBICIDAL USE THEREOF

CROSS-REFERENCE TO RELATED APPLICATIONS

This application is a continuation of copending application Ser. No. 837,957, filed Sept. 29, 1977, which is a continuation of copending application Ser. No. 702,367, filed July 2, 1976, which is a continuation-in-part of application Ser. No. 617,569, filed Sept. 29, 1975, now U.S. Pat. No. 3,979,437, issued Sept. 7, 1976, which is a continuation of application Ser. No. 398,610, filed Sept. 19, 1973, now U.S. Pat. No. 3,941,830, issued Mar. 2, 1976, which is a continuation of application Ser. No. 114,712, filed Feb. 11, 1971, now U.S. Pat. No. 3,784,635, issued Jan. 8, 1974, which is a continuation-in-part of application Ser. No. 819,412, filed Apr. 25, 1969, now U.S. Pat. No. 3,652,645, issued Mar. 28, 1972. Said application Ser. No. 702,367 is also a continuation-in-part of application Ser. No. 545,232 filed Jan. 29, 1975 now U.S. Pat. No. 4,002,662 issued Jan. 11, 1977 which in turn is a continuation-in-part of said application Ser. No. 398,610 filed Sept. 19, 1973 now U.S. Pat. No. 3,941,830, issued May 2, 1976.

BACKGROUND OF THE INVENTION

1. Field of the Invention

This invention is concerned with certain phenoxybenzoic acid compounds and their use as herbicides.

2. Description of the Prior Art

It has been proposed to use as herbicides 2-methoxybenzoic acids (U.S. Pat. No. 3,013,054) and 4-phenoxybenzoic acids (France Pat. No. 1,502,538). It is the discovery of this invention, however, that benzoic acids having a phenoxy substituent in the 5-position are very effective herbicides.

SUMMARY OF THE INVENTION

This invention provides herbicidal compounds having the formula:

[structure: $O_2N$ and $COR$ substituents on a benzene ring linked via $-O-$ to a second benzene ring bearing $(X)_n$]

wherein X is a member selected from the group consisting of hydrogen, halogen (e.g., iodine, fluorine, chlorine and bromine), nitro, trifluoromethyl, cyano, COOH, $$\overset{O}{\underset{\|}{C}}-O-\text{alkyl}$$

(eg. alkyl of 1 to 4 carbon atoms), hydroxy, alkoxy of 1 to 4 carbon atoms, alkyl of 1 to 4 carbon atoms, $$N\diagup^{R_1}_{\diagdown R_2}$$

SH, $SR_1$, $SOR_1$, $SO_2R_1$, $SO_2NH_2$ and combinations thereof, $R_1$ and $R_2$ are selected from the group consisting of alkyl of 1 to 4 carbon atoms, R is selected from the group consisting of hydroxy, alkoxy of 1 to 5 carbon atoms, aryloxy, chloro, amido, alkylamido of 1 to 4 carbon atoms, dialkylamido of 2 to 6 carbon atoms, SH, $SR_1$, and OM in which M is an alkali metal (eg., lithium, sodium and potassium), alkylammonium of 1 to 4 carbon atoms or alkanolammonium of 1 to 4 carbon atoms, n is an integer of 1 to 5, and in which compound at least one X is other than hydrogen; their use as herbicides; and a herbicidal composition comprising at least one of said compounds and a carrier therefor.

DESCRIPTION OF SPECIFIC EMBODIMENTS

The compounds of this invention are readily prepared by the Ullmann ether synthesis reaction between the alkali metal, (eg., Na, K) salt of a suitable substituted phenol and a 5-halo (eg., F, Cl, Br)-2-nitrobenzoic acid or an ester, amide, or salt thereof. The 5-halo-2-nitrobenzoic acid or ester is readily prepared by nitrating a m-halotoluene, followed by oxidation of the methyl group by well-known procedures. Also, the m-halobenzoic acid or ester may be directly nitrated by well-known procedures.

Non-limiting examples of the compounds of this invention are:
propyl 2-nitro-5-(2',4',6'-tribromophenoxy)benzoate;
phenyl 2-nitro-5-(2',4',5'-trifluorophenoxy)benzoate;
2-nitro-5-(2',4',6'-triiodophenoxy)benzoic acid;
2-nitro-5-(2',4',6'-trichlorophenoxy)benzoyl chloride;
2-nitro-5-(2',4',6'-trichlorophenoxy)benzamide;
N-ethyl 2-nitro-5-(2',4',6'-trichlorophenoxy)benzamide;
N-isopropyl 2-nitro-5-(2',4',6'-trichlorophenoxy)benzamide;
N,N-dimethyl 2-nitro-5-(2',4',6', -triclorophenoxy)benzamide;
ethylammonium 2-nitro-5-(2',4',6'-trichlorophenoxy)benzoate;
ethanolammonium 2-nitro-5-(2',4',6'trichlorophenoxy)benzoate;
methyl 2-nitro-5-(2',3', 4', 5',6'-pentachlorophenoxy)benzoate;
n-pentyl 2-nitro-5-(2',4',6'-trichlorophenoxy)benzoate;
2-nitro-5-(2',4'-dichlorophenoxy)benzoic acid;
methyl 2-nitro-5-(2'-chlorophenoxy)benzoate;
methyl 2-nitro-5-(4'-chloro-3'-methylphenoxy)benzoate;
methyl 2-nitro-5-(3'-methylphenoxy)benzoate;
ethyl 2-nitro-5-(2',6'-dichlorophenoxy)benzoate;
isopropyl 2-nitro-5-(2,4'-dichloro-6'-methylphenoxy)benzoate;
ethyl 2-nitro-5-(2'-chloro-4'-fluorophenoxy)benzoate;
2-nitro-5-(2'-chloro-4'-fluorophenoxy)benzoic acid;
methyl 2-nitro-5-(2',4'-dinitrophenoxy)benzoate;
2-nitro-5-(2',4'-dinitrohenoxy)benzoic acid;
2-nitro-5-(2'-chloro-4'-nitrophenoxy)benzoic acid;
isopropyl 2-nitro-5-[3'-(α,α,α-trifluoromethyl)phenoxy]benzoate
isopropyl 2-nitro-5-[3',5'-dicarbomethoxyphenoxy]benzoate;
methyl 2-nitro-5-(2'-methoxyphenoxy)benzoate;
methyl 2-nitro-5-(4'-chloro-2'-nitrophenoxy)benzoate;
2-nitro-5-(2',4'-dichloro-6'-fluorophenoxy)benzoic acid;
methyl 2-nitro-5-(2',4'-dichloro-6'-fluorophenoxy)benzoate;
methyl 2-nitro-5-(2',4'-dicarbomethoxyphenoxy)benzoate;

methyl 2-nitro-5-[2'-cyano-4'-(α,α,α-trifluoromethyl)-phenoxy]benzoate;
methyl 2-nitro-5-(3'-carbomethoxy-4'-hydroxyphenoxy)benzoate;
methyl 2-nitro-5-[4'-chloro-2'-(α,α,α-trifluoromethyl)-phenoxy]benzoate;
methyl 2-nitro-5-(3'-carbomethoxy-4'-nitrophenoxy)-benzoate;
methyl 2-nitro-5-(4'-chloro-2',6'-dibromophenoxy)benzoate;
methyl 2-nitro-5-(2',4'-dicyanophenoxy)benzoate;
methyl 2-nitro-5-[2'-dimethylamino-4'-(α,α,α-trifluoromethyl) phenoxy]benzoate;
ethyl 2-nitro-5-[2'-amino-4'-(α,α,α-trifluoromethyl)-phenoxy]benzoate;
methyl 2-nitro-5-[2'-methyl-4'-methylthiophenoxy]benzoate;
N,N-dimethyl 2-nitro-5[2',6'-dimethyl-4'-methylthiophenoxy]benzamide;
methyl 2-nitro-5-[2'-methyl-4'-methylsulfonylphenoxy]-benzoate;
eThyl 2-nitro-5-[2'-chloro-4'-methylsulfinylphenoxy]-benzoate;
methyl 2-nitro-5-[4'-(N-trifluoromethylsulfonamido)-phenoxy]benzoate
methyl 2-nitro-5-(4'-cyanophenoxy)benzoate;
ethyl 2-nitro-5-(4'-carboethoxyphenoxy)benzoate;
methyl 2-nitro-5-(4'-hydroxyphenoxy)benzoate
2-nitro-5-[2'-t-butylphenoxy]benzoic acid;
2-nitro-5-[2'-carboxyphenoxy]benzoic acid;
methyl 2-nitro-5-(4'-aminophenoxy)benzoate;
methyl 2-nitro-5-(4'-diethylaminophenoxy)benzoate;
methyl 2-nitro-5-(2'-methylaminophenoxy)benzoate;
methyl 2-nitro-5-(4'-mercaptophenoxy)benzoate;
ethyl 2-nitro-5-(4'-methylthiophenoxy)benzoate;
methyl 2-nitro-5-(2'-sulfonamidophenoxy)benzoate;
ethyl 2-nitro-5-(4'methylsulfinYlphenoxy)benzoate;
methyl 2-nitro-5-(4'-methylsulfonylphenoxy)benzoate; and
2-nitro-;b 5-(2',4'-dichlorophenoxy)thiobenzoic acid.

The following example illustrates the preparation of a typical compound of this invention and demonstrates a method for product recovery.

EXAMPLE 1

Methyl 2-nitro-5-(2',4',6'-trichlorophenoxy)benzoate

A stirred solution of methyl 5-chloro-2-nitro-benzoate (17.0 g., 0.079 mole) and the potassium salt of 2,4,6-trichlorophenol (18.6 g., 0.079 mole) in dimethyl sulfoxide (100 ml.) was heated at 90° C. for 17 hours. The cooled reaction mixture was diluted with water (500 ml.) and then extracted with ether (3×100 ml.). The combined ether fractions were washed with 10% sodium hydroxide solution (2×30 ml.) and then with a saturated aqueous chloride solution. The ether solution was dried (Na$_2$SO$_4$) and the solvent evaporated to give a dark oil. Two crystallizations (petroleum ether) gave 1.91 g. of a pale yellow solid, m.p. 101°-103° C.

EXAMPLE 1

IR(nujol):c=o 1723, c—o 1240, and 1260 cm$^{-1}$
NMR (CDCl$_3$):methyl 3.91 ppm (3H), quartet:
6.96 ppm (1H, J=2.5 and 8 c.p.s.), doublet:
7.05 ppm (1H, J=2.5 c.p.s.), broad singlet:
7.05 ppm (2H), and doublet 801 ppm. (1H, J=8 c.p.s.).

EXAMPLES 2 THROUGH 24

Using procedures similar to that described in Example 1, twenty-three other compounds within the scope of this invention were prepared. These compounds are:
(2) 2-nitro-5-(2',4',6'-trichlorophenoxy)benzoic acid, m.p. 184°-189° C.
(3) sodium 2-nitro-5-(2',4',6'-trichlorophenoxy)benzoate m.p. >300° C.
(4) methyl 2-nitro-5-(2',4',5'-trichlorophenoxy)benzoate m.p. 100°-103° C.
(5) methyl 2-nitro-5-(2',4'-dichlorophenoxy)benzoate, m.p. 84°-86° C.
(6) ethyl 2-nitro-5-(2',4',6'-trichlorophenoxy)benzoate, m.p. 60°-64° C.
(7) methyl 2-nitro-5-(2',4'-dibromophenoxy)benzoate, m.p. 98°-100° C.
(8) methyl 2-nitro-5-(4'-chloro-2'-methylphenoxy)benzoate, m.p. 70°-72° C.
(9) methyl 2-nitro-5-(2',4'-dimethylphenoxy)benzoate, oil.
(10) 2-nitro-5-(2',4'-dichlorophenoxy)benzamide, m.p. 130°-133° C.
(11) isopropyl 2-nitro-5-(2',4',6'-trichlorophenoxy)benzoate, m.p. 71°-74° C.
(12) ethyl 2-nitro-5-(2',4'-dichlorophenoxy)benzoate, m.p. 83°-85° C.
(13) isopropyl 2-nitro-5-(2',4'-dichlorophenoxy)benzoate, m.p. 59°-62° C.
(14) methyl 2-nitro-5-(2',4',6'-trichlorophenoxy)thiobenzoate, m.p. 96°-100° C.
(15) methyl 2-nitro-5-(2',4'-dichloro-6'-methylphenoxy)benzoate, m.p. 85°-89° C.
(16) methyl 2-nitro-5-(2'-chloro-4'-fluorophenoxy)benzoate, m.p. 67°-70° C.
(17) isopropyl 2-nitro-5-(2'-chloro-4'-fluorophenoxy)-benzoate, m.p. 48°-51° C.
(18) N-methyl 2-nitro-5-(2',4'-dichlorophenoxy)benzamide, m.p. 137° C.
(19) ethyl 2-nitro-5-(4'-nitrophenoxy)benzoate, m.p. 75°-82° C.
(20) methyl 2-nitro-5-(3'-methyl-4'-nitrophenoxy)benzoate, m.p. 75°-82° C.
(21) isopropyl 2-nitro-5-[2'-nitro-4'-(α, α, α-trifluoromethyl)phenoxy]benzoate oil.
(22) ethyl 2-nitro-5-[2'-nitro-4'-(α, α, α-trifluoromethyl)phenoxy]benzoate, oil.
(23) methyl 2-nitro-5-[2'-chloro-4'-nitrophenoxy]benzoate, m.p. 97°-102° C.
(24) 2-nitro-5-(2'-chloro-4'-nitrophenoxy)benzoic acid, m.p. 185° C.

EXAMPLE 25

2-Nitro-5-[2'-nitro-4'-(α, α, α-trifluoromethyl)phenoxy]benzoic acid

A stirred solution of 4-chloro-3-nitrobenzotrifluoride (22.55 g, 0.1 mole) and the potassium salt of 3-methyl-4-nitrophenol (19.12 g. 0.1 mole) in dimethyl acetamide (75 ml) was heated at 150° for 4 hours. The cooled reaction solution was diluted with water (300ml) to precipitate a brown solid which was filtered and dried to give 28.9 g (85%) of 4-nitro-3-tolyl-2'-nitro-α, α, 60 -trifluoro-4'-tolyl ether, which had an m.p. of 82°-85° C. To a stirred solution of the above diphenyl ether product (25.0 g, 0.073 mole) and sodium dichromate (35.8 g., 0.12 mole) in glacial acetic acid (200 ml) was added concentrated sulfuric acid (60 ml, 1.15 moles) over about 30 minutes. The temperature was maintained below 70° C. during the addition and then raised to 110° C. for 15 hours. The reaction solution was cooled to 60° C. and extracted with hot chloroform. The extract was evaporated to dryness to give an oily solid, which was leached free of starting material with an ether-ligroin mixture. The resulting off-white solid acid weighed 13.6 g (51%), m.p. 185°–187°.

EXAMPLE 26

2-Nitro-5-[2'-nitro-4'-(α,α,α-trifluoromethyl)phenoxy]benzoic acid methyl ester

A stirred solution of the acid from Example 25 (3.5 g, 0.0094 mole) in a 25 wt. %/vol. solution of borontrifluoride in methanol (50 ml) was refluxed for 10 hours. The cooled solution was poured onto water (250 ml) and the resulting oil separated and dried to give 3.4 g (93.5%) of the desired product.

EXAMPLE 27

Methyl 2-nitro-5-(2',4'-dichlorophenoxy) thiobenzoate

Into a solution of 2-nitro-5-(2',4'-dichlorophenoxy) benzoyl chloride (4.16 g., 0.012 mole), prepared from the corresponding acid, in 40 ml. benzene was bubbled methanethiol gas for 0.5 hour at room temperature. The gas bubbling was stopped and the reaction mixture was refluxed for 15 minutes and then cooled. The mixture was diluted with diethyl ether, washed twice with 10% aqueous NaOH, once with NaCl solution, dried, and evaporated to dryness to give 4.3 g. of a oil. Infrared analysis showed a large amount of initial benzoyl chloride was unreacted. The oil was dissolved in 100 ml. benzene and 1.5 g. triethylamine was added. The reaction mixture was heated to 65°–70° C. and methanethiol was bubbled in. There was an immediate precipitate. After 1.5 hours, the reaction mixture was cooled, filtered, and evaporated to dryness to give 4.6 g. of the desired product.

EXAMPLE 28

Ethyl 2-nitro-5-(2',4'-dichlorophenoxy) thiobenzoate

A mixture of 2-nitro-5-(2',4'-dichlorophenoxy) benzoyl chloride (4.16 g., 0.012 mole) and ethanethiol (2.24 g., 0.036 mole) in 40 ml. benzene was heated at reflux for 2 hours and 50 minutes and then cooled. The mixture was diluted with diethyl ether, washed twice with 10% aqueous NaOH, once with NaCl solution, dried, and evaporated to dryness to give 4.2 g. of an oil. Infrared analysis showed a large amount of initial benzoyl chloride and some desired product. The oil was dissolved in 100 ml. benzene and 3.0 g. ethanethiol and about 1.5 g. triethylamine were added. A precipitate formed immediately. The reaction mixture was refluxed for 1.5 hours, cooled, filtered and evaporated to dryness to give 4.65 g. of the desired product.

COMPARATIVE EXAMPLES

A series of compounds were prepared which are position isomers of the compounds of Example 1 through 4. Each compound is designated by the number of the corresponding isomeric compound of Examples 1 through 4, followed by "a" or "b". These compounds are:

(1a) methyl 5-nitro-2-(2',4',6'-trichlorophenoxy) benzoate, m.p. 120°–133° C.

(2a) 5-nitro-2-(2',4',6'-trichlorophenoxy)benzoic acid, m.p. 175°–177° C.

(2b) 4-nitro-2-(2',4',5'-trichlorophenoxy)benzoic acid, m.p. 190°–193° C.

(3a) sodium 5-nitro-2-(2',4',6'-trichlorophenoxy)benzoate, m.p.>300° C.

(4a) methyl 5-nitro-2-(2',4',5'-trichlorophenoxy)benzoate, m.p. 104°–106° C.

(4b) methyl 4-nitro-2-(2',4',5'-trichlorophenoxy)benzoate, m.p. 127°–131° C.

As is apparent from the data in the Table set forth hereinafter, the compounds embodied herein which the nitro group is in the 2-position and the substituted phenoxy group is in the 5-position exhibit markedly higher effectiveness as herbicides than do the comparable compounds in which the nitro group and the substituted phenoxy group are in different positions.

The compounds of this invention can be applied in various ways to achieve herbicidal action. They can be applied, per se. as solids or in vaporized form, but are preferably applied as the toxic components in pesticidal compositions of the compound and a carrier. The compositions can be applied as dusts as liquid sprays, or as gas-propelled sprays and can contain, in addition to a carrier, additives such as emulsifying agents, binding agents, gases compressed to the liquid state, odorants, stabilizers, and the like. A wide variety of liquid and solid carriers can be used. Non-limiting examples of solid carriers include talc, bentonite, diatomaceous earth, pyrophyllite, fullers earth, gypsum, flours derived from cotton seeds and nut shells, and various natural and synthetic clays having a pH not exceeding about 9.5. Non-limiting examples of liquid carriers, include water organic solvents, such as alcohols, ketones, amides and esters; mineral oils, such as kerosene, light oils, and medium oils and vegetable oils, such as cottonseed oil.

In practice, herbicidal application is measured in terms of pounds of herbicide applied per acre. The compounds of this invention are effective herbicides when applied in herbicidal amounts, i.e., at rates between about 0.2 pounds and about 10 pounds per acre.

| HERBICIDAL EFFECTIVENESS Method of Propagating Test Species | |
|---|---|
| Crabgrass | *Digitaria sanguinalis* |
| Yellow Foxtail grass | *Setaria glauca* |
| Johnson grass | *Sorgum Halepense* |
| Barnyard grass | *Echinochloa crus-galli* |
| Amaranth pigweed | *Amaranthus retroflexus* |
| Turnip | *Brassica sp.* |
| Cotton | *Gossypium hirsutum*var. DPL smooth leaf |
| Corn | *Zea Mays* var. Golden Bantam |
| Bean | *Phaseolus vulgaris* var. Black Valentine |

All crop and weed species are planted individually in 3" plastic pots containing potting soil. Four seeds of each of corn, cotton, and snapbeans are seeded to a depth equal to the diameter of the seed. All other species are surface seeded and sprinkled with screened soil in an amount sufficient to cover the seeds. Immediately after planting, all pots are watered by sub-irrigation in greenhouse trays. Pots for the pre-emergence phase are seeded one day before treatment.

Planting dates for the post-emergence phase are varied so that all the seedings will reach the desired state of development simultaneously. The proper state of seedling development for treatment in the post-emergence phase is as follows:

| | |
|---|---|
| GRASSES: | 2 inches in height |
| PIGWEED & TURNIPS: | 1 or 2 true leaves visible above cotyledons. |
| COTTON: | first true leaf 1 inch in length; expanded cotyledons. |
| CORN: | 3 inches - 4 inches in height |
| BEANS: | primary leaves expanded, growing point at primary leaf node. |

METHOD OF TREATMENT

Spray applications are made in a hood containing movable belt and fixed spray nozzle. For passage through the spray hood, one pot of each species (pre-emergence phase) is placed on the forward half of a wooden flat and one pot of established plants (post-emergence phase) is placed on the rear half of the flat. Treatments are moved to the greenhouse after spraying. Watering during the observation period is applied only by sub-irrigation.

Compounds are screened initially at a rate of application equivalent to four or eight pound per acre. Two weeks after treatment the pre- and post-emergence percent effectiveness is visually rated. Subsequent testing is carried out at 2,1 and 0.5 pounds per acre.

Herbicidal testing of the compounds of Examples 1 through 28 and of the comparative compounds provided the results set forth in the Table. The plants are tabulated using the following abbreviations:

| | | | | | |
|---|---|---|---|---|---|
| Crabgrass | CG | Pigweed | PW | | |
| Yellow Foxtail grass | YF | Turnip | TP | | |
| Johnson grass | JG | Cotton | CT | | |
| Barnyard grass | BG | Corn | CN | | |
| Bean | BN | | | | |

TABLE

PRE/POST-EMERGENCE HERBICIDAL ACTIVITY* OF CERTAIN SUBSTITUTED PHENOXYBENZOIC ACIDS AND DERIVATIVES THEREOF

| COMPOUND OF EXAMPLE | COMPOUND CONCENTRATION, LBS./ACRE | CG | YF | JG | BG | PW | TP | CT | CN | BN |
|---|---|---|---|---|---|---|---|---|---|---|
| 1 | 4 | 100/100 | 100/100 | 60/50 | 60/70 | 100/100 | 80/100 | 0/100 | 0/40 | 30/100 |
| | 2 | 100/100 | 80/100 | 30/70 | 20/80 | 100/100 | 0/100 | 90/100 | 30/20 | 70/100 |
| | 1 | 100/90 | 80/100 | 20/60 | 0/60 | 100/100 | 30/90 | 0/100 | 0/20 | 80/100 |
| | 0.5 | 40/50 | 60/80 | 30/60 | 0/40 | 100/70 | 0/80 | 40/20 | 0/20 | 30/70 |
| 1a(Comparative) | 4 | 20/20 | 0/20 | 0/20 | 0/20 | 20/0 | 0/30 | 100/0 | 50/0 | 20/80 |
| 2 | 4 | 70/70 | —/— | 70/90 | 60/70 | —/— | 100/100 | 0/100 | 0/70 | 80/70 |
| 2a(Comparative) | 4 | 20/30 | 0/20 | 20/30 | 0/20 | —/20 | 30/90 | 50/20 | 0/0 | 50/70 |
| 2b(Comparative) | 4 | 0/30 | 40/0 | 50/30 | 20/20 | 20/20 | 0/50 | 40/20 | 30/30 | 80/0 |
| 3 | 4 | 50/80 | —/— | 30/60 | 40/60 | —/— | 95/100 | 50/100 | 0/40 | 50/100 |
| 3a(Comparative) | 4 | 0/20 | 0/20 | 0/20 | 0/20 | 50/50 | 0/60 | 100/0 | 30/0 | 50/40 |
| 4 | 4 | 90/60 | —/— | 80/90 | 50/50 | —/— | 40/70 | 80/70 | 0/50 | 80/80 |
| 4a(Comparative) | 8 | 30/30 | 0/20 | 20/30 | 0/20 | 30/30 | 40/0 | 0/30 | 0/0 | 60/0 |
| 4b(Comparative) | 4 | 20/20 | 0/20 | 0/20 | 0/20 | 0/20 | 0/60 | 30/50 | 0/30 | 0/60 |
| 5 | 4 | 100/95 | —/— | 90/90 | 90/90 | —/— | 80/100 | 50/80 | 0/40 | 50/100 |
| 6 | 4 | 100/80 | —/— | 80/90 | 50/70 | 100/100 | 40/90 | 30/100 | 0/100 | 100/100 |
| 7 | 8 | 80/60 | —/— | 50/40 | 60/50 | 100/100 | 20/100 | 30/90 | 0/50 | 100/100 |
| 8 | 8 | 50/60 | —/— | 20/30 | 0/20 | 100/100 | 0/40 | 0/40 | 0/30 | 100/100 |
| 9 | 8 | 30/30 | —/— | 0/40 | 20/20 | 90/90 | 20/50 | 0/70 | 0/40 | 100/90 |
| 10 | 4 | 80/70 | —/— | 40/40 | 40/30 | 100/100 | 20/70 | 100/40 | 0/20 | 100/100 |
| 11 | 4 | 60/70 | —/— | 30/60 | 20/50 | 90/100 | 0/50 | 30/70 | 0/30 | 80/60 |
| 12 | 8 | 90/90 | —/— | 90/90 | 60/90 | 100/100 | 0/100 | 0/100 | 0/70 | 0/100 |
| | 4 | 100/90 | —/— | 90/100 | 60/60 | 100/100 | 0/100 | 30/90 | 0/70 | 30/100 |
| | 2 | 100/100 | 100/— | 40/60 | 80/70 | —/100 | 30/100 | 80/70 | 0/70 | 100/100 |
| | 1 | 100/100 | —/— | 40/90 | 50/80 | —/— | 30/100 | 20/80 | 0/20 | 50/80 |
| 13 | 8 | 70/90 | —/— | 30/90 | 20/80 | 90/100 | 0/30 | 30/70 | 0/20 | 100/100 |
| 14 | 4 | 70/80 | —/— | 20/90 | 0/40 | 100/100 | 70/100 | 90/90 | 20/20 | 0/80 |
| 15 | 8 | 100/100 | 100/— | 50/70 | 50/— | —/100 | 70/90 | 0/90 | 0/30 | 50/100 |
| | 4 | 90/90 | 0/— | 40/60 | 0/60 | —/— | 60/90 | 100/60 | 0/40 | 0/100 |
| | 2 | 90/70 | —/— | 30/40 | 20/70 | —/— | 70/60 | 0/60 | 0/50 | 0/100 |
| 16 | 8 | 100/90 | 100/100 | 80/100 | 100/90 | 100/100 | 100/100 | 40/100 | 80/40 | 80/100 |
| | 4 | 100/100 | 100/100 | 80/80 | 80/80 | 100/100 | 70/100 | 40/90 | 20/80 | 80/100 |
| | 2 | 100/100 | 100/100 | 90/100 | 80/90 | 100/100 | 80/100 | 30/90 | 0/80 | 0/90 |
| | 0.8 | 90/60 | 100/80 | 70/50 | 40/50 | 100/100 | 40/100 | 80/60 | 30/20 | 50/100 |
| 17 | 8 | 100/40 | 90/40 | 70/40 | 50/30 | 100/100 | 0/60 | 0/80 | 0/30 | 0/90 |
| | 4 | 100/100 | 100/100 | 80/90 | 50/70 | 100/100 | 0/40 | 0/50 | 0/30 | 0/90 |
| | 2 | 100/90 | 100/90 | 30/90 | 30/90 | 100/100 | 20/30 | 0/50 | 0/30 | 0/90 |
| | 1 | 60/50 | 100/80 | 90/60 | 20/30 | 100/100 | 0/40 | 90/30 | 30/0 | 80/80 |
| 18 | 8 | 90/80 | —/— | 60/80 | 70/40 | —/— | 90/100 | 30/80 | 0/80 | 0/100 |
| 19 | 10 | 40/30 | —/— | 90/— | —/— | —/— | 0/90 | —/60 | —/— | —/60 |
| 20 | 10 | 50/20 | —/— | 90/— | —/— | —/— | 20/20 | —/30 | —/— | —/40 |
| 21 | 3 | 100/— | 100/—10-0/— | 30/— | —/— | 50/— | 30/— | 0/— | 0/— | |
| 22 | 1 | 90/— | 100/— | 100/— | 30/— | —/— | 30/— | 50/— | 60/— | 0/— |
| 23 | 10 | 80/— | 100/— | 100/— | 30/— | —/— | 80/— | —/— | —/— | —/— |
| 24 | 10 | 100/— | —/— | 30/— | —/— | —/— | 100/— | —/— | —/— | —/— |
| 25 | 8 | 80/60 | 90/100 | 50/40 | 30/60 | 100/100 | 100/100 | 30/50 | 0/30 | 30/90 |
| 26 | 8 | 100/80 | 100/90 | 40/20 | 90/60 | 100/100 | 90/90 | 0/50 | 0/20 | 70/90 |
| | 4 | 100/90 | 100/100 | 70/90 | 80/50 | 100/100 | 100/100 | 0/50 | 0/20 | 0/90 |
| | 2 | 90/70 | 100/100 | 60/60 | 40/70 | 100/100 | 90/90 | 0/50 | 0/30 | 0/90 |
| 27 | 8 | 20/30 | 80/— | —/— | —/— | —/— | 100/100 | —/100 | —/— | —/100 |

TABLE-continued
PRE/POST-EMERGENCE HERBICIDAL ACTIVITY* OF CERTAIN SUBSTITUTED PHENOXYBENZOIC ACIDS AND DERIVATIVES THEREOF

| COMPOUND OF EXAMPLE | COMPOUND CONCENTRATION, LBS./ACRE | CG | YF | JG | BG | PW | TP | CT | CN | BN |
|---|---|---|---|---|---|---|---|---|---|---|
| 28 | 8 | 0/30 | —/— | —/— | —/— | —/— | 100/100 | —/100 | —/— | —/100 |

*Herbicidal activity is measured in per cent effectiveness

Although the present invention has been described with preferred embodiments, it is to be understood that modifications and variations may be resorted to without departing from the spirit and scope of this invention, as those skilled in the art will readily understand. Such modifications and variations are considered to be within the purview and scope of the appended claims.

What is claimed is:

1. Herbicidal compounds having the formula:

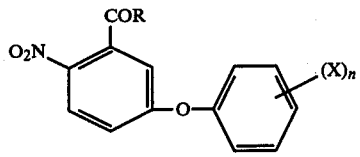

wherein X is a member selected from the group consisting of halogen, nitro trifluoromethyl, cyano, COOH,

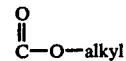

(alkyl of 1 to 4 carbon atoms), hydroxy, alkoxy of 1 to 4 carbon atoms,

SH, $SR_1$, $SOR_1$, $SO_2R_1$, $SO_2NH_2$ and combinations thereof, $R_1$ and $R_2$ are selected from the group consisting of alkyl of 1 to 4 carbon atoms, R is alkoxy of 1 to 5 carbon atoms, n is an integer of 1 to 5.

2. The method for controlling plant growth that comprises applying an herbicidal amount of a compound defined in claim 1.

3. An herbicidal composition comprising a carrier for an herbicide and an herbicidal amount of a compound defined in claim 1.

* * * * *

UNITED STATES PATENT AND TRADEMARK OFFICE
CERTIFICATE OF CORRECTION

Page 1 of 3

PATENT NO. : 4,164,410
DATED : August 14, 1979
INVENTOR(S) : ROBERT J. THEISSEN

It is certified that error appears in the above-identified patent and that said Letters Patent are hereby corrected as shown below:

Column 1, line 67, $SO_2NH_2$and   space needed before "and"

Column 2, line 35, "triclorophenoxy" should be --trichlorophenoxy--

Column 2, line 55, "dinitrohenoxy" should be --dinitrophenoxy"

Column 3, line 23, "eThyL" should be --ethyl--

Column 3, line 38, "methylsulfinYlphenoxy" should be --methylsulfinylphenoxy--

Column 3, line 41, "2-nitro-;b 5" should be --2-nitro-5--

Column 3, line 67, "801" should be --8.01--

Column 4, line 46, comma (,) should appear before "oil"

Column 4, line 63, "60" should be --$\alpha$--

Column 5, line 68, "120°" should be --128°--

Column 6, line 12, "herein which" should be --herein in which--

Column 6, line 20, "per se." should be --per se,--

UNITED STATES PATENT AND TRADEMARK OFFICE
CERTIFICATE OF CORRECTION

Page 2 of 3

PATENT NO. : 4,164,410
DATED : August 14, 1979
INVENTOR(S) : ROBERT J. THEISSEN

It is certified that error appears in the above-identified patent and that said Letters Patent are hereby corrected as shown below:

| | |
|---|---|
| Column 6, line 23, | "dusts" should have a comma (,) following |
| Column 6, line 34, | "water" should have ";" following |
| Column 8, line 5, | "pound" should be --pounds-- |
| Table, Example 21 at 3 lbs. under YF | "100/-10-" should be --100/- -- and below that delete "0/-" |
| Table, Example 21 at 3 lbs. under JG | "30/-" should be --100/- -- |
| Table, Example 21 at 3 lbs. under BG | "-/-" should be --30/- -- |
| Table, Example 21 at 3 lbs. under PW | "50/-" should be -- -/- -- |
| Table, Example 21 at 3 lbs. under TP | "30/-" should be --50/- -- |

UNITED STATES PATENT AND TRADEMARK OFFICE
CERTIFICATE OF CORRECTION

PATENT NO. : 4,164,410
DATED : August 14, 1979
INVENTOR(S) : ROBERT J. THEISSEN

It is certified that error appears in the above-identified patent and that said Letters Patent are hereby corrected as shown below:

Table, Example 21 at 3 lbs. under CT     "0/-" should be --30/- --

Table, Example 21 at 3 lbs. under BN     insert --0/- --

Signed and Sealed this

Fifteenth Day of January 1980

[SEAL]

Attest:

SIDNEY A. DIAMOND

Attesting Officer     Commissioner of Patents and Trademarks